US00PP37574P2

(12) United States Plant Patent
Heuger

(10) Patent No.: US PP37,574 P2
(45) Date of Patent: Aug. 11, 2026

(54) ***HELLEBORUS* PLANT NAMED 'HL 1066'**

(50) Latin Name: ***Helleborus* x *niger* X *Helleborus* x *hybridus***
Varietal Denomination: HL 1066

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 19/397,973

(22) Filed: Nov. 23, 2025

(51) Int. Cl.
*A01H 5/02* (2018.01)
*A01H 6/72* (2018.01)

(52) U.S. Cl.
USPC ..... Plt./439

(58) Field of Classification Search
None
See application file for complete search history.

(56) References Cited

U.S. PATENT DOCUMENTS

PP32,340 P2 * 10/2020 Heuger ..... A01H 5/02
Plt./439

* cited by examiner

*Primary Examiner* — Susan McCormick Ewoldt
(74) *Attorney, Agent, or Firm* — C. Anne Whealy

(57) ABSTRACT

A new and distinct cultivar of *Helleborus* plant named 'HL 1066', characterized by its upright to outwardly spreading and mounded plant habit; moderately vigorous to vigorous growth habit; dark green-colored leaflets; freely flowering habit; flowers with pinkish white to pale purple-colored petals and white and pale purple-colored sepals; and good garden performance.

2 Drawing Sheets

Figure 1:
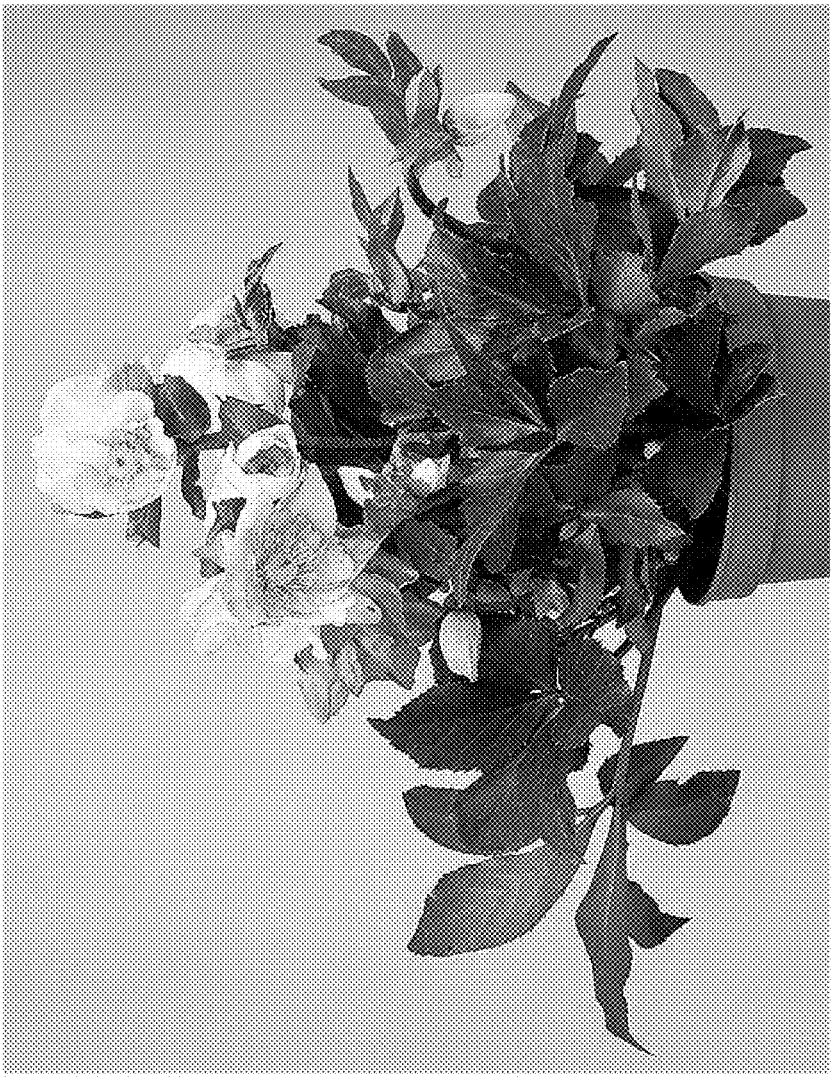

Botanical designation: *Helleborus* x *niger* X *Helleborus* x *hybridus*.

Cultivar denomination: 'HL 1066'.

CROSS-REFERENCED TO CLOSELY-RELATED APPLICATIONS

A European Community Plant Breeder's Rights application for the instant plant was filed by the Inventor/Applicant, Mr. Josef Heuger of Glandorf, Germany, on Nov. 30, 2024, application number 2024/2907. Foreign priority is not claimed to this application.

A United Kingdom Plant Breeder's Rights application for the instant plant was filed by the Inventor/Applicant, Mr. Josef Heuger of Glandorf, Germany, on Aug. 29, 2025, application number 30/990. Foreign priority is not claimed to this application.

BACKGROUND OF THE INVENTION

The present invention relates to a new and distinct cultivar of *Helleborus* plant, botanically known as *Helleborus* x *niger* X *Helleborus* x *hybridus* and hereinafter referred to by the name 'HL 1066'.

The new *Helleborus* plant is a product of a planned breeding program conducted by the Inventor in Glandorf, Germany. The objective of the breeding program was to create new uniform *Helleborus* plants with unique leaf and flower coloration and tolerance to biotic and abiotic stresses.

The new *Helleborus* plant originated from a cross-pollination conducted by the Inventor in Glandorf, Germany in December, 2017 of a proprietary selection of *Helleborus* x *niger* identified as code number 001, not patented, as the female, or seed, parent and a proprietary selection of *Helleborus* x *hybridus* identified as code number 16-19, not patented, as the male, or pollen, parent. The new *Helleborus* plant was discovered and selected by the Inventor as a single flowering plant from within the progeny of the stated cross-pollination grown in a controlled greenhouse environment in Glandorf, Germany in November, 2019.

Asexual reproduction of the new *Helleborus* plant by in vitro axillary meristem culture in a controlled environment in Glandorf, Germany since October, 2020 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'HL 1066'. These characteristics in combination distinguish 'HL 1066' as a new and distinct *Helleborus* plant:

1. Upright to outwardly spreading and mounded plant habit.
2. Moderately vigorous to vigorous growth habit.
3. Dark green-colored leaflets.
4. Freely flowering habit.
5. Flowers with pinkish white to pale purple-colored petals and white and pale purple-colored sepals.
6. Good garden performance.

Plants of the new *Helleborus* differ from plants of the female parent selection in the following characteristics:

1. Petals of plants of the new *Helleborus* are not transformed into nectaries whereas petals of plants of the female parent selection are transformed into nectaries.
2. Flower sepals of plants of the new *Helleborus* are white to pale purple in color whereas flower sepals of plants of the female parent selection are white in color.

Plants of the new *Helleborus* differ from plants of the male parent selection in the following characteristics:

1. Petals of plants of the new *Helleborus* are not transformed into nectaries whereas petals of plants of the male parent selection are transformed into nectaries.
2. Flower sepals of plants of the new *Helleborus* are white to pale purple in color whereas flower sepals of plants of the male parent selection are pink in color.

Plants of the new *Helleborus* can also be compared to plants of *Helleborus* x *niger* X *Helleborus* x *hybridus* 'COSEH 5900', disclosed in U.S. Plant Pat. No. 32,340. In side-by-side comparisons, plants of the new *Helleborus* differ primarily from plants of 'COSEH 5900' in the following characteristics:

1. Petals of plants of the new *Helleborus* are not transformed into nectaries whereas petals of plants of 'COSEH 5900' are transformed into nectaries.
2. Flower sepals of plants of the new *Helleborus* are white to pale purple in color whereas flower sepals of plants of 'COSEH 5900' are white in color.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet (FIG. 1) is a side perspective view of a typical flowering plant of 'HL 1066' grown in a container.

Figure 2:
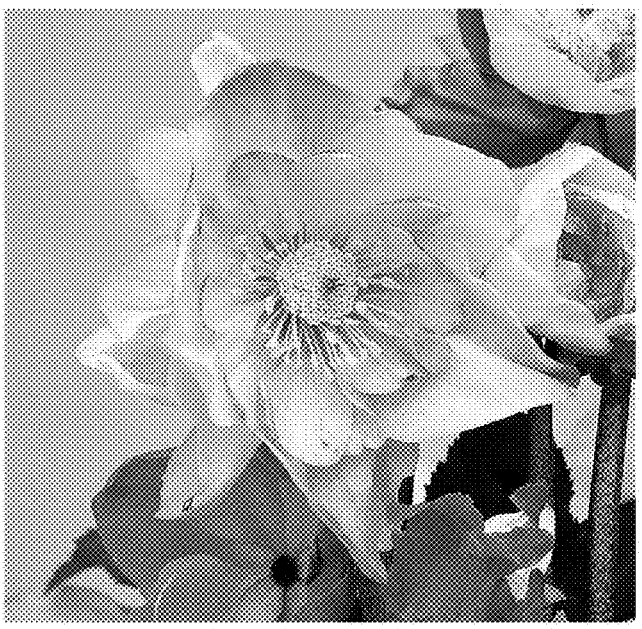

The photograph at the top of the second sheet (FIG. 2) is a close-up view of a typical flower of 'HL 1066'.

Figure 3:
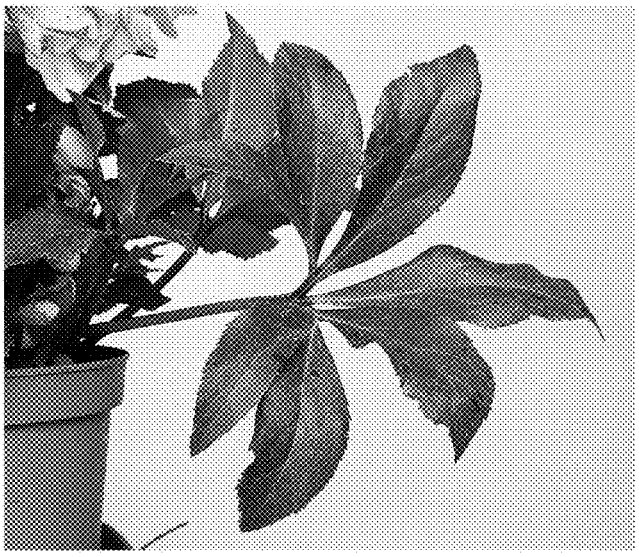

The photograph at the bottom of the second sheet (FIG. 3) is a close-up view of typical leaflets of 'HL 1066'.

DETAILED BOTANICAL DESCRIPTION

The aforementioned photographs and following observations, measurements and values describe plants grown during the winter in 17-cm containers in a glass-covered greenhouse in Glandorf, Germany and under cultural practices typical of commercial *Helleborus* production. During the production of the plants, day temperatures ranged from 12° C. to 32° C. and night temperatures ranged from 5° C. to 12° C. Plants were 48 weeks old when the photographs were taken and 14 months old when the detailed description was taken. In the following description, color references are made to The Royal Horticultural Society Colour Chart, Sixth Edition (2019 reprint), except where general terms of ordinary dictionary significance are used.

Botanical classification: *Helleborus* x *niger* X *Helleborus* x *hybridus* 'HL 1066'.

Parentage:

*Female, or seed, parent*.—Proprietary selection of *Helleborus* x *niger* identified as code number 001, not patented.

*Male, or pollen, parent*.—Proprietary selection of *Helleborus* x *hybridus* identified as code number 16-19, not patented.

Propagation:

*Type*.—In vitro axillary meristem culture.

*Time to initiate roots, winter*.—About 55 days at temperatures about 12° C.

*Time to produce a rooted young plant, winter*.—About 170 days at temperatures ranging from about 4° C. to 15° C.

*Root description*.—Thick to thin, fleshy; typically white to brownish in color, actual color of the roots is dependent on substrate composition, water quality, fertilizer type and formulation, substrate temperature and physiological age of roots.

*Rooting habit*.—Low branching; sparse.

Plant description:

*Plant and growth habit*.—Herbaceous perennial; upright to outwardly spreading and mounding plant habit with flowers held above the foliar plane; plant shape, roughly flattened globular to globular; moderately vigorous to vigorous growth habit and moderate growth rate.

*Plant height, soil level to top of foliar plane*.—About 22.9 cm.

*Plant height, soil level to top of flowers*.—About 34.9 cm.

*Plant diameter* (*area of spread*).—About 43 cm.

Leaf description:

*Arrangement*.—Leaves arranged in basal rosettes; leaves palmately compound with typically five leaflets per leaf.

*Leaf length*.—About 14.3 cm.

*Leaf width*.—About 18.5 cm.

*Leaflet length*.—About 10.3 cm.

*Leaflet width*.—About 5.2 cm.

*Leaf shape*.—Palmate; roughly reniform in outline.

*Leaflet shape*.—Broadly elliptic to broadly elliptic-obovate; half of the lowest leaflets are cleft.

*Leaflet apex*.—Acute.

*Leaflet base*.—Attenuate.

*Leaflet margin*.—Serrate; slightly to moderately coarsely undulate.

*Leaflet texture and luster, upper and lower surfaces*.—Smooth, glabrous; coriaceous and tough; slightly glossy.

*Leaflet venation pattern*.—Pinnate and reticulate.

*Leaflet color*.—Developing leaflets, upper surface: Close to 137B; at the base, close to 183A and 183B. Developing leaflets, lower surface: Close to 146B; main veins, close to 183C. Fully developed leaflets, upper surface: Close to a blend of 147A and N189A; at the base, tinged with close to 200C; venation, close to 144A and 144B. Fully developed leaflets, lower surface: Close to 147B; venation, close to 145A.

*Petioles*.—Length: About 14.5 cm. Diameter: About 5.5 mm by 6 mm. Strength: Strong. Texture and luster, upper and lower surfaces: Smooth, glabrous; slightly glossy. Color, upper surface: Close to 146B with fine dots, close to 200B. Color, lower surface: Close to 146C with fine dots, close to 200B and 200C.

Flower description:

*Flower shape and habit*.—Double rotate bowl-shaped flowers arranged in panicles; freely flowering habit with about three flowers per inflorescence and about 66 flowers and flower buds per plant; flowers face outwardly to slightly nodding.

*Fragrance*.—None detected.

*Natural flowering season*.—Plants begin flowering about ten months after planting; plants flower naturally from early winter into the late winter in Germany.

*Flower longevity on the plant*.—About ten days; sepals persistent, other flower parts are not persistent.

*Flower buds*.—Length: About 2.4 cm. Diameter: About 1.5 cm. Shape: Narrowly ovate. Texture and luster: Smooth, glabrous; matte to slightly glossy. Color: Close to 150D; at the base, close to 145B.

*Inflorescence height* (*including peduncle*).—About 31.8 cm.

*Inflorescence diameter*.—About 11.7 cm.

*Flower diameter*.—About 10 cm.

*Flower depth*.—About 3.7 cm.

*Petals*.—Quantity and arrangement: About 12 to 16, arranged in a single whorl. Length: About 4 cm. Width: About 2 cm. Shape: Obovate to elliptic. Apex: Obtuse to bluntly acute. Base: Attenuate. Margin: Entire; not undulate. Texture and luster, upper surface: Smooth, glabrous; matte. Texture and luster, lower surface: Smooth, glabrous; slightly glossy. Color: When opening, upper surface: Close to 76D; towards the apex and margins, close to 76C; venation, close to N75D. When opening, lower surface: Close to 76B; towards the apex, flushed with close to 72B. Fully opened, upper surface: Close to a blend of 76D and N155B; towards the apical margins, close to 76B; venation, close to N75D; with subsequent development, color becoming closer to a blend of 145B and 145C. Fully opened, lower surface: Close to 76D; towards the apex, flushed with close to 76A; with subsequent development, color becoming closer to a blend of 145B and 145C.

*Sepals*.—Quantity and arrangement: About five, arranged in a single whorl. Length: About 5.4 cm. Width: About 4.6 cm. Shape: Broadly ovate to broadly elliptic; slightly concave. Apex: Broadly and bluntly acute to obtuse. Base: Cuneate. Margin: Entire. Texture and luster, upper surface: Smooth, glabrous; matte. Texture and luster, lower surface: Smooth, glabrous; slightly glossy. Color: When opening, upper surface: Close to NN155A; towards the apex and margins, slightly flushed with close to 75B; at the base, close to 145B. When opening, lower surface: Close to N155B flushed with close to NN74B and NN74C; at the base, close to 145B. Fully opened, sepals, upper surface: Close to NN155B; towards the apex and margins, slightly flushed with close to 76C; at the base, close to 145B. Fully opened, lower surface: Close to N155B flushed with close to NN74C; at the base, close to 145B.

*Flower bracts*.—Quantity per flower: Typically one or two. Length: About 5.4 cm. Width: About 3.5 cm. Shape: Ovate, occasionally with one or two shallow lobes. Apex: Acute to tri-lobed. Base: Truncate to cuneate. Margin: Entire and distally, serrate; slightly coarsely undulate. Color, upper surface: Close to 137A. Color, lower surface: Close to a blend of 146B and 147B.

*Peduncles*.—Length: About 26.6 cm. Diameter: About 6 mm. Aspect: About 20° from vertical. Strength: Strong. Texture and luster: Smooth, glabrous; moderately glossy. Color: Close to 146D; moderately to heavily covered with fine dots, close to 187B.

*Pedicels*.—Length: About 3.9 cm. Diameter: About 3.5 mm. Aspect: About 35° from peduncle axis. Strength: Moderately strong. Texture and luster: Smooth, glabrous; moderately glossy. Color: Close to 146D; heavily covered with fine dots, close to 187C.

*Reproductive organs*.—Stamens: Quantity per flower: About 140.Filament length: About 1.7 cm. Filament color: Close to 155C. Anther shape: Double and broadly reniform; basifixed. Anther size: About 2 mm by 3 mm. Anther color: Close to 150C. Pollen amount: Sparse. Pollen color: Close to 4D. Pistils: Quantity per flower: About two to seven. Pistil length: About 1 cm. Stigma diameter: About 0.3 mm. Stigma shape: Club-shaped. Stigma color: Close to 157D. Style length: About 0.95 cm. Style color: Close to 184D. Ovary color: Close to 150C. Seeds and fruits: To date, seed and fruit development have not been observed on plants of the new *Helleborus*.

Garden performance: Plants of the new *Helleborus* have been observed to have good garden performance and to tolerate rain, wind, high temperatures about 35° C. and to be suitable for USDA Hardiness Zones 5 through 9.

Pathogen & pest resistance: To date, plants of the new *Helleborus* have not been observed to be resistant to pathogens and pests common to *Helleborus* plants.

It is claimed:

1. A new and distinct *Helleborus* plant named 'HL 1066' as herein illustrated and described.

* * * * *